(12) United States Patent
Qiu et al.

(10) Patent No.: US 11,534,518 B2
(45) Date of Patent: Dec. 27, 2022

(54) STERILIZATION LAMP MODULE INTEGRATED IN VEHICLE AND VEHICLE COMPRISING A STERILIZATION LAMP MODULE

(71) Applicant: Volvo Car Corporation, Gothenburg (SE)

(72) Inventors: Lijun Qiu, Shanghai (CN); Heng Zhao, Shanghai (CN); Yong Chen, Shanghai (CN)

(73) Assignee: Volvo Car Corporation, Gothenburg (SE)

( * ) Notice: Subject to any disclaimer, the term of this patent is extended or adjusted under 35 U.S.C. 154(b) by 219 days.

(21) Appl. No.: 16/928,050

(22) Filed: Jul. 14, 2020

(65) Prior Publication Data

US 2021/0023251 A1 Jan. 28, 2021

(30) Foreign Application Priority Data

Jul. 26, 2019 (CN) .......................... 201910683473.9

(51) Int. Cl.
| | |
|---|---|
| *A61L 2/10* | (2006.01) |
| *A61L 2/24* | (2006.01) |
| *B60Q 9/00* | (2006.01) |
| *B60S 1/64* | (2006.01) |
| *B60Q 3/54* | (2017.01) |

(52) U.S. Cl.
CPC ................... *A61L 2/24* (2013.01); *A61L 2/10* (2013.01); *B60Q 9/00* (2013.01); *B60S 1/64* (2013.01); *A61L 2202/11* (2013.01); *A61L 2202/14* (2013.01); *A61L 2202/25* (2013.01); *B60Q 3/54* (2017.02)

(58) Field of Classification Search
CPC .......... A61L 2/24; A61L 2/10; A61L 2202/11; A61L 2202/14; A61L 2202/25
See application file for complete search history.

(56) References Cited

U.S. PATENT DOCUMENTS

| | | | |
|---|---|---|---|
| 4,245,550 A | 1/1981 | Suzuki et al. | |
| 9,149,548 B2 * | 10/2015 | Davis | ......................... A61L 2/10 |
| 9,855,353 B1 * | 1/2018 | Stacy | ......................... A61L 2/10 |

(Continued)

FOREIGN PATENT DOCUMENTS

| | | |
|---|---|---|
| CN | 210454406 U | 5/2020 |
| DE | 102015117859 A1 | 4/2016 |

(Continued)

OTHER PUBLICATIONS

Dec. 4, 2020 Partial European Search Report Issued on International Application 20186960.

*Primary Examiner* — Wyatt A Stoffa

(74) *Attorney, Agent, or Firm* — Clements Bernard Walker; Christopher L. Bernard

(57) ABSTRACT

An integrated sterilization lamp module integrated in a vehicle, including: a sterilization lamp which is configured for emitting sterilization light rays to sterilize surfaces in the vehicle at which they arrive; an attachment device which is configured for attaching the integrated sterilization lamp module to the vehicle; and an automatic controller which is configured for controlling the sterilization lamp so that it can automatically perform a sterilization operation. The application also relates to a vehicle including the integrated sterilization lamp module.

9 Claims, 3 Drawing Sheets

(56) References Cited

U.S. PATENT DOCUMENTS

| | | | | |
|---|---|---|---|---|
| 10,046,076 B1* | 8/2018 | Collins | ...................... | A61L 9/20 |
| 2005/0077482 A1* | 4/2005 | Poppi | ........................ | A61L 2/10 |
| | | | | 250/492.1 |
| 2008/0310996 A1* | 12/2008 | Kim | .......................... | A61L 9/20 |
| | | | | 422/186.3 |
| 2009/0191100 A1* | 7/2009 | Deal | .......................... | A61L 2/10 |
| | | | | 422/105 |
| 2009/0314308 A1* | 12/2009 | Kim | ...................... | A61L 2/0088 |
| | | | | 134/1 |
| 2011/0274582 A1* | 11/2011 | Davis | ........................ | A61L 2/10 |
| | | | | 280/78 |
| 2015/0062893 A1* | 3/2015 | Lynn | .......................... | F21V 7/00 |
| | | | | 362/231 |
| 2015/0090903 A1* | 4/2015 | Cole | .......................... | A61L 2/24 |
| | | | | 250/492.1 |
| 2016/0089459 A1* | 3/2016 | Boodaghians | ............ | A61L 9/20 |
| | | | | 250/492.1 |
| 2016/0367711 A1* | 12/2016 | Zulyniak | ................. | H01H 35/00 |
| 2017/0049915 A1* | 2/2017 | Brais | .................... | H05B 47/115 |
| 2018/0065126 A1 | 3/2018 | Abate et al. | | |
| 2019/0091738 A1* | 3/2019 | Chen | .................. | B60H 1/00742 |
| 2020/0140292 A1* | 5/2020 | Schowalter | ............... | A61L 2/26 |
| 2022/0088246 A1* | 3/2022 | Dayton | ...................... | A61L 2/10 |

FOREIGN PATENT DOCUMENTS

| | | |
|---|---|---|
| JP | 20120254673 A | 12/2012 |
| WO | 20170200761 A1 | 11/2017 |

* cited by examiner

STERILIZATION LAMP MODULE INTEGRATED IN VEHICLE AND VEHICLE COMPRISING A STERILIZATION LAMP MODULE

CROSS-REFERENCE TO RELATED APPLICATION

The present application claims priority to CN Patent Application No. 201910683473.9 filed on Jul. 26, 2019, the disclosure of which is hereby incorporated by reference in its entirety.

TECHNICAL FIELD

The present application relates to the field of vehicles, and in particular to a sterilization lamp module integrated in a vehicle and a vehicle including the sterilization lamp module.

BACKGROUND

Nowadays, more and more original equipment manufacturers (OEMs) of vehicles have paid their attention to problems caused by serious air pollution, for example, caused by increasingly haze days with over-high PM indexes. In consideration of customers' interests and benefits as well as improvement of their own brand competitiveness, OEMs are paying more and more attention to purification of air and improvement of air quality within the vehicles. In order to purify the air within the vehicles, for example, the air conditioning systems of the vehicles are designed to have air pollutant filtering function to reduce the PM index of the air within the vehicles. One such example is nano air conditioners installed in the vehicles for air purification.

However, using the air conditioning system to perform air purification operations in the vehicle for a period of time may lead to an interior space of the vehicle having a relatively high humidity condition, which may cause a variety of bacteria to grow in the vehicle. This may cause health problems to an occupant in the vehicle and it may also damage related components of the vehicle or shorten their service lives. At present, there is no solution to prevent bacterial growth in the vehicle.

UV disinfection is a common method of eliminating bacteria that grow in the air. Portable ultraviolet sterilization lamps are available in the current automotive market. This type of portable UV sterilization lamp can be powered with a USB interface in the vehicle, which is often referred to as "plug and play". In practice, the ultraviolet sterilization lamp is held in a user's hand to sterilize the internal space of the vehicle, which requires the user to be at a close distance and the user is most likely to be exposed to the ultraviolet light rays. This type of device is harmful to the user's health, and moreover, the reliability and safety of such ultraviolet sterilization lamps are not satisfactory.

SUMMARY

An object of the application is to provide an integrated sterilization lamp module in a vehicle, which can automatically perform a sterilization operation when there is no occupant in the vehicle. The invention does not have to be held with a user's hand to manually operate, which fundamentally eliminates any potential harm to the user's health.

To this end, in one aspect of the application, an integrated sterilization lamp module in a vehicle is provided, which includes: a sterilization lamp, which is configured for emitting sterilization light rays to sterilize surfaces in the vehicle onto which the sterilization light rays are projected; an attachment device, which is configured for attaching the integrated sterilization lamp module to the vehicle; and an automatic controller, which is configured for controlling the sterilization lamp so that it can automatically perform a sterilization operation.

In an embodiment, the integrated sterilization lamp module is attached to a roof lining of the vehicle or along a rooftop interior of the vehicle by the attachment device.

In an embodiment, the integrated sterilization lamp module further includes a damper, which is configured for providing dampening and cushioning protection for the sterilization lamp.

In an embodiment, the damper includes silicone members provided over the sterilization lamp at opposite ends of the sterilization lamp.

In an embodiment, the integrated sterilization lamp module further includes a reflector, which is configured for reflecting the sterilization light rays emitted from the sterilization lamp toward the roof of the vehicle, back to an interior of the vehicle to sterilize the surfaces within the vehicle.

In an embodiment, the reflector is provided, at a reflective surface that faces the interior of the vehicle, with a reflective coating.

In an embodiment, the integrated sterilization lamp module further includes an indicator indicating whether the sterilization lamp is performing the sterilization operation, wherein the indicator has a first state indicating that the sterilization lamp is performing the sterilization operation and a second state indicating that the sterilization lamp is not performing the sterilization operation.

In an embodiment, the integrated sterilization lamp module further includes a lampshade, wherein the sterilization light rays emitted from the sterilization lamp is irradiated onto the surfaces to be sterilized through the lampshade.

In an embodiment, the lampshade includes a peripheral portion and a central portion, the central portion being formed with grooves extending in an extending direction of the sterilization lamp.

In an embodiment, the integrated sterilization lamp module further includes: a frame; and leaf springs, each of the leaf springs including a substantially plate-shaped base portion and a curved portion extending from the base portion, wherein, at opposite ends of the sterilization lamp, fasteners are inserted through holes formed in a lug of the reflector, holes formed in the base portion of the leaf spring, holes formed in the peripheral portion of the lampshade, and holes formed in the frame, to package the sterilization lamp within a space formed by these components to form a modular unit.

In an embodiment, the attachment structure is defined by the curved portion.

In an embodiment, the automatic controller is integrated into an electronic control unit of the vehicle.

In another aspect of the application, a vehicle including at least one integrated sterilization lamp module is provided, wherein the sterilization lamp module is being detachably or permanently attached to a roof lining of the vehicle or along a rooftop interior of the vehicle.

DESCRIPTION OF EMBODIMENTS

Figure 1:
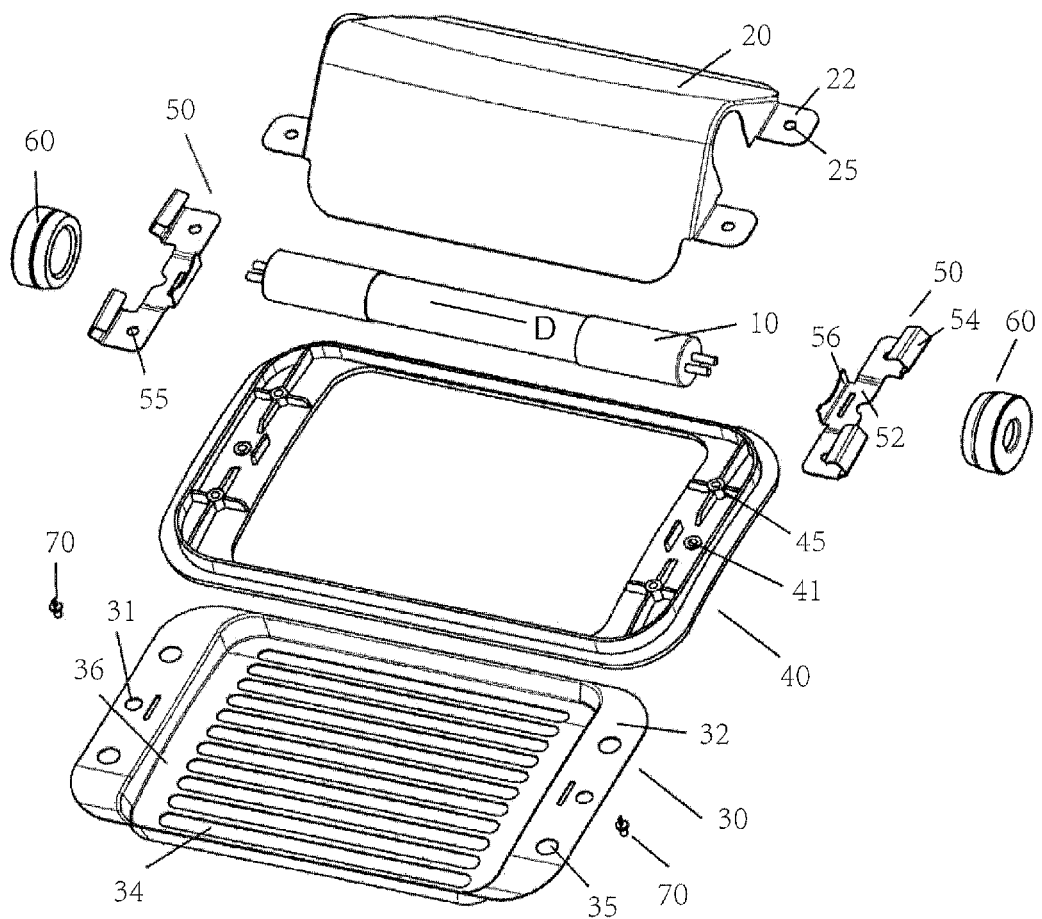
FIG. 1 shows an exploded view of an integrated sterilization lamp module in accordance with one embodiment of the present application.
Figure 2:
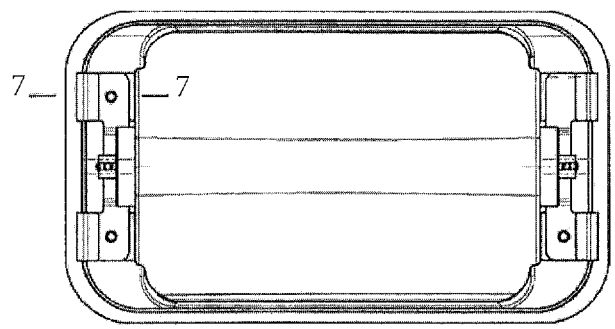
FIGS. 2-5 show a plane view, a side view, a front view, and a bottom perspective view, respectively, of the integrated sterilization lamp module of FIG. 1 in an assembled state.
Figure 3:
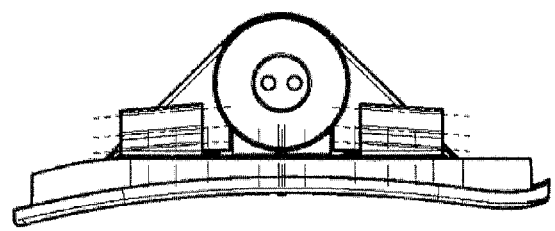
Figure 4:
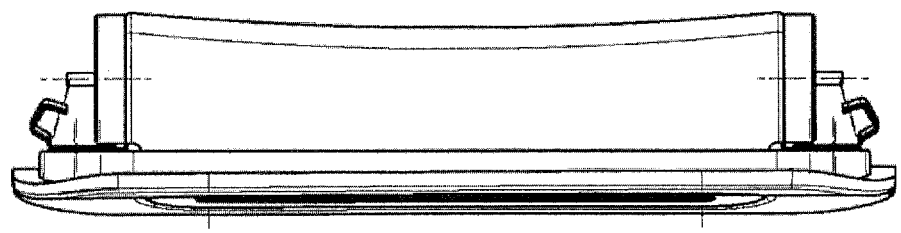
Figure 5:
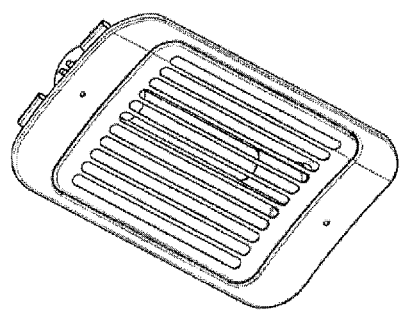

An integrated sterilization lamp module according to one embodiment of the present application can be mounted or integrated at a suitable location in a vehicle, and for example mounted to a roof lining of the vehicle. Preferably, the location at which the integrated sterilization lamp module is mounted or attached can be selected or arranged to the roof lining or to be along a rooftop interior of the vehicle so that the sterilization lamp can sterilize as large surface range or area as possible within the vehicle. It will be understood by those skilled in the art that, according to actual needs, the vehicle may include a plurality of integrated sterilization lamp modules of the present application, to sterilize different surfaces in different ranges or to sterilize some surfaces more thoroughly with sterilization light rays projected from different angles. For example, one or more of the sterilization lamp modules are mounted to the roof to emit the sterilization light rays in an up-to-down direction to sterilize surfaces they reach, and/or one or more of the sterilization lamp modules are mounted at a rear or side of an interior of the vehicle to sterilize certain surfaces in the vehicle that cannot be sterilized by the sterilizing lamp modules mounted to the roof.

In particular, the integrated sterilization lamp module according to one aspect of the present application mainly includes a sterilization lamp, an automatic controller for controlling automatic operations of the sterilization lamp, and an attachment structure for integrating the sterilization lamp to the roof.

According to one embodiment of the present application, the sterilization lamp can be any type of sterilization lamp or tube known in the art. An example is a common ultraviolet sterilization lamp, which uses ultraviolet light rays to kill viruses on an object surface, such as bacterial propagules, spores, mycobacteria, coronavirus, fungi, *rickettsia*, and *chlamydia*. In the present application, the "object surface" may be any surface within the vehicle, including surfaces that may be touched by an occupant, such as seat surfaces, floor surfaces, door or window surfaces, exposed surfaces of a steering wheel and of an instrument in the front of the vehicle etc., and any other surfaces the sterilization light rays can reach. As an example, the sterilization lamp can have a sterilization wavelength in a range of 200 nm to 500 nm, and preferably 200 nm to 300 nm. More preferably, the sterilization lamp can have a sterilization wavelength of about 265 nm, which ensures a thorough sterilization as well as convenience and safety. According to one embodiment of the present application, the sterilization lamp can include a tube wall made of quartz glass, and the tube wall can have a thickness increased to 1 mm to enhance an anti-vibration effect.

The automatic controller of the integrated sterilization lamp module according to one embodiment of the present application is configured for automatically controlling or activating the sterilization lamp to start a sterilization operation. In particular, the automatic controller can be configured so that a user can set at least one or, for example, more parameters of the sterilization operation: sterilization preparation and preheating duration, duration of each sterilization operation, start time of the sterilization lamp, etc. In one embodiment, the sterilization preparation and preheating duration of the sterilization lamp can be set to be approximately 5 minutes, the duration of each sterilization operation of the sterilization lamp can be set to be approximately 5 minutes, a work frequency of the sterilization lamp can be set to be once a day, and the start time of the sterilization lamp can be scheduled to be 2 am every day, and so on. In another embodiment, the start time of the sterilization lamp can be set to be after a predetermined period of time when the vehicle engine is turned off, or can be set to be at midnight every day, for example, at 2 am every day, so as to ensure that the sterilization operation is performed when there is no occupant in the vehicle. In this way, not only safety of the occupant but also daily or regular sterilization of the vehicle is ensured. In yet another embodiment, the vehicle is provided with an occupant presence detector and the automatic controller is configured for activating the sterilization lamp only when the occupant presence detector detects that no occupant is in the vehicle. In an alternative embodiment, the user can set the automatic controller according to his or her preference or according to actual situations, to ensure that the sterilization lamp can only perform the automatic sterilization operation when no occupant is in the vehicle. Preferably, the automatic controller can be integrated into an electrical control system of the vehicle, such as an electronic control unit (ECU) of the vehicle or can be provided as a control unit dedicated to this function.

The attachment structure of the integrated sterilization lamp module according to the present application can be configured as any feasible mechanical structure which can integrate the module to the vehicle. In this application, the meaning of "integration" includes detachable fixation or attachment, where the sterilization lamp module can be detached from one position and removably re-assembled to another position in the vehicle, as well as permanent fixation or attachment, where the sterilization lamp module is attached to a fixed position in the vehicle and un-detachable. Specifically, the attachment of the sterilization lamp module to the vehicle includes the following attachment methods: screw connection, snap connection, plug connection, interference connection, riveting, welding, hooking, and the like.

Figure 6:
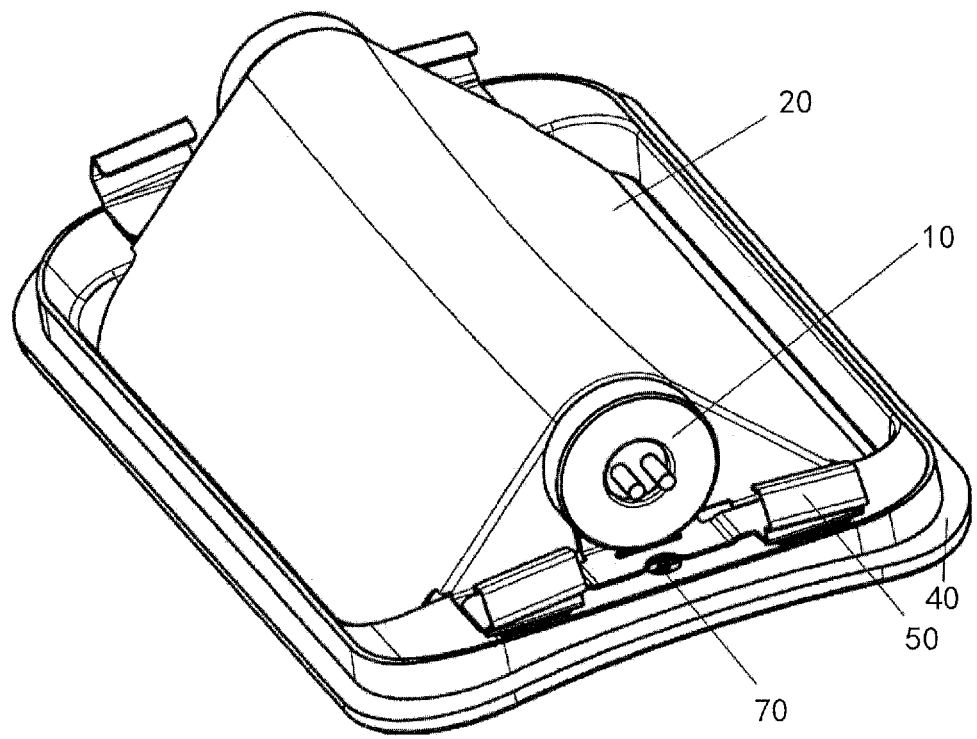
FIG. 6 shows another three-dimensional perspective view of the integrated sterilization lamp module of FIG. 1 in the assembled state.

A feasible structure of an integrated sterilization lamp module according to the present application is described below with reference to FIGS. 1-7, wherein FIG. 1 shows an exploded view of a structure of an exemplary integrated sterilization lamp module, FIGS. 2-5 show a top view, a side view, a front view, and a bottom perspective view of the module in an assembled state, respectively, and FIG. 6 shows another three-dimensional perspective view of the module.

In the drawings, a sterilization lamp of the integrated sterilization lamp module is indicated by a reference sign 10, and the sterilization lamp defines an extension direction D (FIG. 1). In addition to the sterilization lamp 10, the exemplary integrated sterilization lamp module further includes a reflector 20, which is configured for reflecting sterilization light rays emitted from the sterilization lamp 10 toward a roof of a vehicle back to an interior of the vehicle; a lampshade 30, which is configured for allowing the sterilization light rays to pass through to sterilize or disinfect surfaces to be sterilized in the vehicle; a substantially rectangular frame 40 and leaf springs 50; a damper 60, which is configured for providing shock absorbing and cushioning functions to the sterilizing lamp; and at least one indicator 70.

According to one embodiment of the present application, the reflector 20 can be shaped and sized to reflect as much light rays, which are emitted from the sterilization lamp 10 toward the roof, as possible and to concentrate the reflected light rays. In the example shown in the drawings, in a cross section perpendicular to the extending direction D of the sterilization lamp 10, the reflector 20 has a curved shape like a parabola or quadratic curve to increase a reflection angle of the sterilized light rays to the greatest extent and maximizes a range to be sterilized. The reflector 20 can be made of any suitable material such as plastic. Further, the reflector 20 can be coated with a reflective layer on its surface facing the sterilization lamp 10 to improve the reflection.

According to one embodiment of the present application, the lampshade 30 can be made of any light transmissive material such as quartz glass. In another embodiment, the lampshade 30 can be formed by a stainless steel mesh. In yet another alternative embodiment, the lampshade 30 can be made of a PMMA material, due to its high light transmittance and due to its properties of not harming the occupant in the vehicle even if/when the sterilization lamp is damaged or jostled. Preferably, the lampshade 30 includes a peripheral portion 32 and a central portion 36, which includes grooves 34 extending in the extending direction D of the sterilization lamp 10, wherein the groove 32 is configured for allowing as much sterilizing light rays as possible to pass through. While allowing the sterilization light rays to pass though, the lampshade 30 also provides a function of protecting the sterilization lamp 10 and provides an overall aesthetic appearance. It should be understood by those skilled in the art that the "lampshade" in the present application is not limited to any particular form, shape or structure. It includes any type of covering member that performs the similar function as the lampshade 30 described above, or can be any covering member that at least partially or completely covers the sterilization lamp module.

According to one embodiment of the present application, the damper 60 may be made of any suitable material, for example an elastic material such as silica gel. In the illustrated embodiment, the damper 60 is configured as ring members fitted over the sterilizing lamp 10 at its opposite ends. The frame 40 has a generally rectangular shape. Two leaf springs 50 are disposed at the opposite ends of the sterilization lamp 10 in the extending direction D, respectively. The leaf spring 50 includes a substantially plate-shaped base portion 52, a curved portion 54 extending from the base portion 52, and a convex portion 56 extending from the base portion 52 and configured for supporting the damper.

Figure 7:
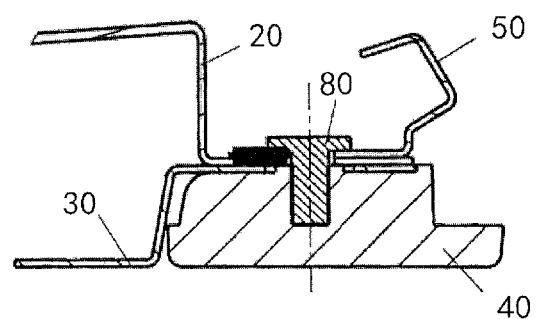
FIG. 7 is a partially enlarged cross-sectional view taken along a line 7-7 in FIG. 2.

During the process of assembling the integrated sterilizing lamp module according to one embodiment of the present application, screws 80 (FIG. 7) are inserted through holes 55 formed in the base portion 52 of the leaf spring 50, holes 25 formed in lugs 22 of the reflector 20, holes 35 formed in the peripheral portion 32 of the lampshade 30, and holes 45 formed in the frame 40, to package the sterilization lamp 10 and the ring members as the damper at both ends of the sterilization lamp 10 within a space defined by the reflector 20, the lampshade 30, and the frame 40, forming a modular unit as shown in FIG. 7.

In the assembled module, each of the two ring members as the damper 60 fitted over the sterilizing lamp 10 at its ends is supported in a substantially arcuate recess formed in the convex portion 56 of each of the leaf springs 50. The curved portion 54 of the leaf spring 50 is used to attach the present sterilization lamp module to the vehicle, and in particular, the curved portion 54 can be snapped into a mating slot (not shown) of the vehicle roof.

In the illustrated embodiment, two indicators 70 are included, which are mounted by means of respective holes 41 and 31, which are at opposite ends of the frame 40 and the lampshade 30, respectively. As an example, the indicator 70 can be an indicator light or any other known type of indicator. For example, the indicator 70 can have a first state indicating that the sterilization lamp 10 is performing the sterilization operation and a second state indicating that the sterilization lamp 10 is not performing the sterilization operation. The first state and the second state can be on and off states, respectively. Optionally, the indicator can also include any form of sound indicator.

The sterilization lamp for emitting the sterilization light rays further includes an automatic controller for controlling the sterilization lamps to perform automatic sterilization operations, and the attachment structure for attaching the module to the vehicle. The integrated sterilization lamp module according to one aspect of the present application is configured for automatically sterilizing the surfaces inside the vehicle when there is no occupant in the vehicle and avoids any harm to a human body caused by the sterilization operation. The exemplary structure of the present application further includes the reflector, which is configured for maximizing utilization of the sterilized light rays emitted from the sterilization lamp, further includes a lampshade, which is configured for allowing the sterilization light rays to pass through and providing an aesthetical appearance for the module, and further includes the indicators for the purpose of providing visual or audible warnings or indications.

The embodiments shown in the drawings and described above are provided for the purposes of illustration and description, and are not intended to limit the scope of the application. Modifications or equivalent substitutions to the structural details, forms, etc., can be made by persons of ordinary skill in the art after reading this application, without departing from the scope of the application as defined by the appended claims.

The invention claimed is:

1. An integrated sterilization lamp module in a vehicle, comprising:
   a sterilization lamp configured for emitting sterilization light rays to sterilize surfaces in the vehicle onto which the sterilization light rays are projected;
   an attachment device configured for attaching the integrated sterilization lamp module to the vehicle;
   a controller configured for controlling the sterilization lamp so that it can perform a sterilization operation;
   a reflector which is configured for reflecting the sterilization light rays which are emitted from the sterilization lamp toward the roof of the vehicle, back to an interior of the vehicle to sterilize the surfaces within the vehicle; and
   a lampshade through which the sterilization light rays emitted from the sterilization lamp being irradiated onto the surfaces to be sterilized,
   wherein the lampshade comprises a peripheral portion and a central portion, the central portion being formed with grooves extending in an extending direction of the sterilization lamp, wherein integrated sterilization lamp module further comprises:
a frame; and
leaf springs, each of the leaf springs comprising a substantially plate-shaped base portion and a curved portion extending from the base portion,
wherein, at opposite ends of the sterilization lamp, fasteners are inserted through holes formed in a lug of the reflector, holes formed in the base portion of the leaf spring, holes formed in the peripheral portion of the lampshade, and holes formed in the frame, to package the sterilization lamp within a space formed by these components to form a modular unit.

2. The integrated sterilization lamp module of claim 1, wherein the integrated sterilization lamp module is attached to a roof lining of the vehicle or along a rooftop interior of the vehicle by the attachment device.

3. The integrated sterilization lamp module of claim 1, further comprising a damper configured for providing dampening and cushioning protection for the sterilization lamp.

4. The integrated sterilization lamp module of claim 3, wherein the damper comprises silicone members provided over the sterilization lamp at opposite ends of the sterilization lamp.

5. The integrated sterilization lamp module of claim 1, wherein the reflector is provided, at a reflective surface that faces the interior of the vehicle, with a reflective coating.

6. The integrated sterilization lamp module of claim 1, further comprising an indicator indicating whether the sterilization lamp is performing the sterilization operation, wherein the indicator has a first state indicating that the sterilization lamp is performing the sterilization operation and a second state indicating that the sterilization lamp is not performing the sterilization operation.

7. The integrated sterilization lamp module of claim 1, wherein the attachment structure is defined by the curved portion.

8. The integrated sterilization lamp module of claim 1, wherein the controller is integrated into an electronic control unit of the vehicle.

9. A vehicle comprising at least one integrated sterilization lamp module according to claim 1, the sterilization lamp module being detachably or permanently attached to a roof lining of the vehicle or along a rooftop interior of the vehicle.

* * * * *